United States Patent
Eck et al.

(10) Patent No.: US 7,485,397 B2
(45) Date of Patent: Feb. 3, 2009

(54) REUSABLE PRINTING PLATE, PRINTING PRESS AND PRINTING UNIT HAVING THE PRINTING PLATE, PROCESS FOR IMAGING THE PRINTING PLATE AND PROCESS FOR PREPARATION OF A FLUORINATED ORGANIC PHOSPHONIC ACID

(75) Inventors: Wolfgang Eck, Bar Harbor, ME (US); Martin Gutfleisch, Dossenheim (DE); Gerhard Daniel Peiter, Viernheim (DE); Matthias Schlörholz, Heidelberg (DE)

(73) Assignee: Heidelberger Druckmaschinen AG, Heidelberg (DE)

( * ) Notice: Subject to any disclaimer, the term of this patent is extended or adjusted under 35 U.S.C. 154(b) by 13 days.

(21) Appl. No.: 11/183,575

(22) Filed: Jul. 18, 2005

(65) Prior Publication Data

US 2006/0040210 A1    Feb. 23, 2006

(30) Foreign Application Priority Data

Jul. 16, 2004    (DE) .................... 10 2004 034 581

(51) Int. Cl.
*G03F 7/00*    (2006.01)
*G03F 7/004*    (2006.01)

(52) U.S. Cl. .................... 430/19; 430/302; 430/401; 430/494; 101/478

(58) Field of Classification Search .................. 430/19, 430/401, 494, 322, 323; 101/478
See application file for complete search history.

(56) References Cited

U.S. PATENT DOCUMENTS

| | | | |
|---|---|---|---|
| 6,321,652 B1 | 11/2001 | Fujinami et al. | |
| 6,824,882 B2 * | 11/2004 | Boardman et al. | .......... 428/457 |
| 6,851,364 B1 | 2/2005 | Suda | |
| 2003/0031860 A1 | 2/2003 | Hotta et al. | |
| 2004/0007146 A1 * | 1/2004 | Gutfleisch et al. | ........ 101/401.1 |

FOREIGN PATENT DOCUMENTS

| | | |
|---|---|---|
| DE | 102 27 054 A1 | 12/2003 |
| EP | 1 084 863 A1 | 3/2001 |
| EP | 1 247 644 A2 | 10/2002 |

* cited by examiner

*Primary Examiner*—Amanda C. Walke
(74) *Attorney, Agent, or Firm*—Laurence A. Greenberg; Werner H. Stemer; Ralph E. Locher

(57) ABSTRACT

A reusable printing plate, in particular for use both in wet offset printing and in dry offset printing, includes a printing area and a metal oxide surface treated with at least one fluorinated phosphonic acid. A printing press and a printing unit having the printing plate, a process for imaging the printing plate and a process for preparation of a fluorinated organic phosphonic acid are also provided.

9 Claims, 4 Drawing Sheets

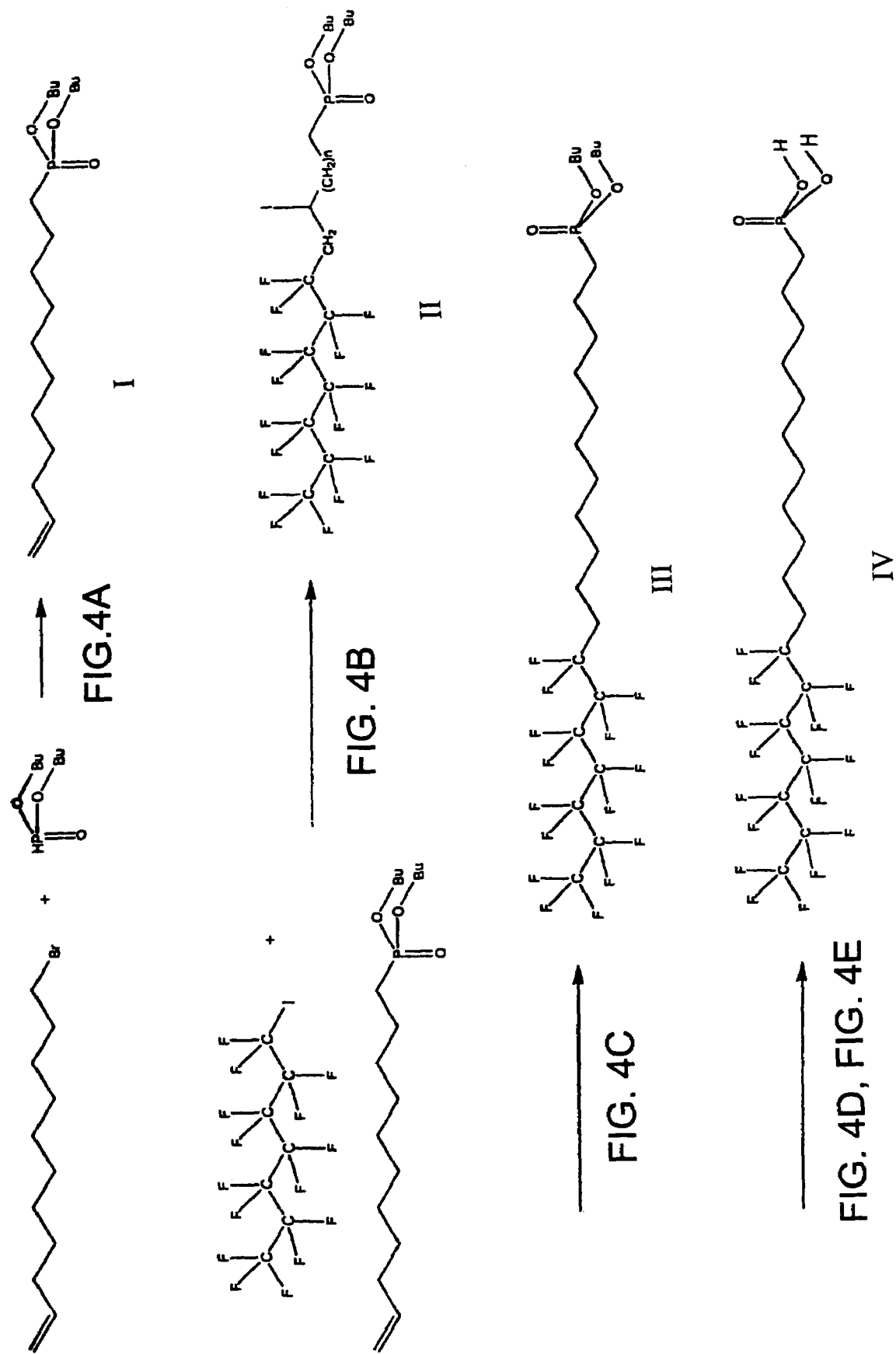

REUSABLE PRINTING PLATE, PRINTING PRESS AND PRINTING UNIT HAVING THE PRINTING PLATE, PROCESS FOR IMAGING THE PRINTING PLATE AND PROCESS FOR PREPARATION OF A FLUORINATED ORGANIC PHOSPHONIC ACID

BACKGROUND OF THE INVENTION

Field of the Invention

The invention relates to a reusable printing plate, in particular for use both in wet offset printing and in dry offset printing, having a printing area. The invention also relates to a printing press and a printing unit having the printing plate. The invention furthermore relates to a process for imaging of a reusable printing plate. The invention additionally relates to a process for the preparation of a fluorinated phosphonic acid, in particular for the treatment of a reusable printing plate.

Printing plates are used in printing units of printing presses to apply a predetermined print pattern, a predetermined subject or image to a print medium. Typical print media are paper, board, cardboard, organic polymers, textiles or the like.

Printing plates on whose printing area, a part of the surface of the printing plate, the pattern to be printed is permanently applied, structured or written are predominantly used. The printing plate can be used only once. For various reasons, it is desirable to use printing plates which can be used repeatedly, in particular written on repeatedly or imaged repeatedly. In other words, printing areas which can be erased after structuring in a first image and subsequently can be structured in a second image are of particular interest. In the context of this description, a reusable printing plate is understood as meaning a printing plate having a printing area which can be structured repeatedly in various images.

In conventional offset printing, structuring of the printing area is present in regions of different wetting properties, in particular hydrophilic/lipophobic and hydrophobic/lipophilic regions.

Wet offset printing (also: conventional offset printing) is based on the utilization of the immiscibility of lipophilic substances, in particular of oily fluids or liquids, and hydrophilic substances, in particular of aqueous fluids or liquids, on the printing plate, the lipophilic substance or the ink or printing ink being held by the image-producing regions and the hydrophilic substance or water being held by the non-image-producing regions of the printing area.

If the printing area prepared in a suitable manner is wetted with hydrophilic and lipophilic substances, the non-image regions preferably retain the hydrophilic substance and repel the lipophilic substance, while the image regions accept the lipophilic substance and repel the hydrophilic substance. Consequently, the lipophilic substance is then transferred in a suitable matter to the surface of a material on which the image is to be fixed.

Dry offset printing (also: waterless offset printing) is based on structuring of the printing area in regions of different wetting properties. A printing plate surface which is initially ink-repellent over its whole area, i.e. lipophobic, becomes imagewise ink-accepting in the course of the structuring, i.e. becomes lipophilic, so that, on application of printing ink to the surface, the printing ink adheres only to the imaged, ink-accepting regions of the surface and is transferred directly or indirectly from there to the print medium.

In European Patent Application EP 1 084 863 A1, corresponding to U.S. Pat. No. 6,851,364, the surface of a substrate which includes titanium oxide is erased over its whole area through the use of UV radiation and structured through the use of IR radiation in the course of imaging.

German Published, Non-Prosecuted Patent Application DE 102 27 054 A1, corresponding to U.S. Patent Application Publication No. 2004/0007146, describes a reusable printing plate, for example for use in wet offset printing, which has a printing area treated with at least one amphiphilic organic compound and in the form of a metal oxide surface, the polar region of the amphiphilic organic compound having an acid-like character.

In U.S. Pat. No. 6,321,652 B1, a molecular layer including self-arranging molecules whose terminal groups can be modified in their hydrophobic properties is applied to a substrate in the course of imaging.

The process time for the preparation, i.e. the preparation of a reusable printing plate for a subsequent imaging process, is a critical parameter in preparation of the printing plate in the printing press since continuous printing is not possible during this time, at least with the printing unit involved in the preparation process. It is therefore desirable to shorten the process time for the preparation compared with the prior art.

There is still a demand for printing plates which can be used or employed both in wet offset printing and in dry offset printing.

There is moreover a demand for printing plates which have greater tolerance with respect to defects on printing areas occupied by amphiphilic molecules.

SUMMARY OF THE INVENTION

It is accordingly an object of the invention to provide a reusable printing plate, a printing press and a printing unit having the printing plate, a process for imaging the printing plate and a process for preparation of a fluorinated organic phosphonic acid, which overcome the hereinafore-mentioned disadvantages of the heretofore-known devices and methods of this general type, which provide a printing area that permits repeated production and erasing of images and in which a process time for the preparation has a short duration.

It is a further object or alternative object of the invention to provide a reusable printing plate which can be used or employed both in wet offset printing and in dry offset printing.

It is a further or alternative object of the invention to provide a reusable printing plate which has greater tolerance with respect to defects on printing areas occupied by amphiphilic molecules.

A further or alternative object of the invention is to provide a process for imaging of a reusable printing plate, which process makes it possible to produce and to erase images repeatedly on the printing plate with a short process time for the preparation.

It is a further or alternative object of the invention to provide a process for imaging of a reusable printing plate, the printing plate imaged by the process being capable of being used or employed both in wet offset printing and in dry offset printing.

A further or alternative object of the invention is to provide a process for the preparation of a fluorinated phosphonic acid, through the use of which, in particular, a reusable printing plate can be treated.

With the foregoing and other objects in view there is provided, in accordance with the invention, a reusable printing plate having a printing area, comprising a metal oxide surface treated with at least one fluorinated phosphonic acid whereby the printing plate is capable of use both in wet offset printing and in dry offset printing. The fluorinated phosphonic acid is preferably an organic fluorinated alkylphosphonic acid having 8 to 30 carbon atoms, for example a semiperfluorinated alkylphosphonic acid or a (partly) aromatic phosphonic acid.

A reusable printing plate according to the invention, in particular for use both in wet offset printing and in dry offset printing, having a printing area, is distinguished by the fact that the printing area has a metal oxide surface treated with at least one fluorinated phosphonic acid.

The reusable printing plate according to the invention can particularly advantageously be used in an offset printing process, in particular in direct or in indirect lithographic printing. It can therefore also be referred to in particular as a rewriteable offset printing plate or as an offset printing plate which is recoatable (in the nano range).

The reusable printing plate according to the invention can furthermore particularly advantageously be used both in wet offset printing and in dry offset printing.

The treated printing area is rendered hydrophobic and lipophilic by the fluorinated phosphonic acid for conventional offset ink when used in wet offset printing or becomes lipophobic for dry offset printing ink when used in dry offset printing.

According to a preferred embodiment, the fluorinated phosphonic acid is present as a fluorinated alkylphosphonic acid, a semiperfluorinated alkylphosphonic acid or a (partly) aromatic phosphonic acid. The term "partly aromatic" is to be understood in this Application as meaning that a segment of the relevant molecule, in particular a carbon chain, or a plurality of segments of the relevant molecule, has aromatic character.

According to a further preferred embodiment, the fluorinated phosphonic acid has a carbon chain, in particular a singly or multiply branched carbon chain, the number of carbon atoms being greater than or equal to 8 and less than or equal to 30.

According to a further preferred embodiment, the metal oxide surface may be a naturally oxidized titanium surface, a naturally oxidized stainless steel surface, for example Hastelloy, naturally oxidized aluminum surface, titanate ($TiO_2$) or zirconate ($ZrO_2$).

The invention is therefore based, inter alia, on the concept of treating technically rough or smooth metal oxide surfaces with fluorinated phosphonic acid, in particular of applying fluorinated phosphonic acid to technically wet or smooth metal oxide surfaces or of coating technically rough or smooth metal oxide surfaces with fluorinated phosphonic acid (here, "technically rough" means that the RMS value is $\geq 80$ nm, and "technically smooth" means that the RMS value is <80 nm, where the RMS value specifies a root mean square value of the roughness).

The reusable printing plate can also be referred to in particular as a printing plate which is recoatable (in the nano range).

With the aid of fluorinated phosphonic acid, it is possible to produce, in a reproducible defined manner, hydrophobic (for wet offset printing) or lipophobic metal oxide surfaces (for dry offset printing), in particular titanium oxide surfaces.

The metal oxide surface is brought into a hydrophobic, ink-carrying state which can serve as an initial state for imaging for a wet offset printing process. The contact angle, measured relative to water, of these hydrophobic metal oxide surfaces have values from the number set of the range of real numbers between 80 and 120 degrees. The metal oxide surface can then be brought into a hydrophilic, ink-carrying state by controlled supply of energy. The contact angles, measured relative to water, in the hydrophilic state have values from the number set of the range of real numbers between 0 and 10 degrees.

The difference between the two states is therefore sufficiently large for wet offset printing (in the case of technically rough or smooth surfaces). The printing plate according to the invention can therefore be changed over, in particular between a hydrophilic and a hydrophobic state. After structuring of the rewriteable printing plate according to the invention in regions in the hydrophilic state and regions in the hydrophobic state, a wet offset printing process can be carried out.

The printing plate according to the invention can also be changed over for use in dry offset printing, in particular between a lipophobic and lipophilic state with respect to a dry offset printing ink (in the case of technically smooth surfaces).

The reusable printing plate according to the invention can be designed with different topological and geometrical properties in different embodiments. The printing plate according to the invention can be realized as a surface of a solid cylinder or as a surface of a hollow cylinder. The cylinder, solid or hollow, may be in particular a straight circular cylinder. Surface is to be understood as meaning in particular the lateral surface.

Alternatively, the printing plate according to the invention may also be in the form of a sleeve, a plate or a sheet. A sleeve has two surfaces (inner surface and outer surface) and has two edges. The sleeve may be cylindrical with a uniform diameter, in particular internal diameter or external diameter, (hollow circular cylinder) or conical, i.e. with variable, in particular uniformly increasing or decreasing diameter, in particular internal diameter or external diameter. Internal diameter and external diameter may vary in different ways. It is therefore not a simply assembled object in the topological sense. A plate has two surfaces (top and bottom) and has one edge. In the topological sense, it is therefore a simply assembled object. The plate may be in particular cuboid or rectangular. The sheet can be stored in the rolled up state in the interior of a cylinder and can be drawn or further wound onto the surface of the cylinder in the circumferential direction.

With the objects of the invention in view, it is also provided that the reusable printing plate according to the invention may be used in a printing unit, in particular in an offset printing unit. It may form the surface of a printing cylinder or may be held on the surface of a cylinder.

A printing unit according to the invention is therefore distinguished by at least one reusable printing plate according to the invention.

With the objects of the invention in view, it is additionally provided that the printing unit according to the invention may be part of a printing press, in particular of an offset printing press. The printing press may be a sheet-processing or a web-processing printing press. A sheet-processing printing press may have a feeder, a number of printing units and a delivery. A printing press according to the invention has at least one printing unit according to the invention.

With the objects of the invention in view, there is also provided, associated with the reusable printing plate, a process for imaging of a reusable, in particular rewriteable or recoatable, printing plate having various advantageous further developments.

The process according to the invention is based on the desire to provide a circular process in which a printing plate according to the invention can be repeatedly imaged and erased so that the printing plate is suitable in particular for offset printing. The process, according to the invention, for imaging can be carried out both inside and outside a printing unit or a printing press. The printing area can be processed imagewise by exposure through a mask-like transparency. However, point-by-point direct exposure with digital information is preferred.

A process according to the invention, for imaging of a reusable printing plate is distinguished by:
preparation of a reusable printing plate having a printing area as described above with reference to a printing plate according to the invention;
production of an image on the printing plate by selective point-by-point supply of energy; and
erasing of the image after printing on a print medium, in particular in an offset printing process, by supply of energy over a large area.

The rewriteable printing plate can be designed as described in more detail above in this description.

An image is produced by selective, point-by-point supply of energy, in particular point-by-point supply of energy which is selective with respect to space and time, on the printing area. In other words, digital imaging is carried out. As a result of the imaging, the printing plate is converted from a hydrophobic into a hydrophilic state (in wet offset printing) or from a lipophobic into a lipophilic state (in dry offset printing).

According to a preferred embodiment, the process is furthermore distinguished by the fact that the preparation of the reusable printing plate includes the wetting of the printing area with a solution which contains at least one fluorinated phosphonic acid.

The process can be iterated or repeated. The steps of preparation, imaging and erasing can therefore be carried out repeatedly with different print patterns or subjects. The process according to the invention therefore permits a circular process.

The printing area can be wetted with an aqueous solution or with an alcoholic solution, in particular ethanol, which contains at least one fluorinated phosphonic acid in suitable concentration, preferably in the concentration of 1 mmol/l. In an advantageous further development, this coating or finishing can be effected in an ultrasonic bath. The application, finishing or coating of the metal oxide surface, in particular titanium dioxide surface, with the molecules of the fluorinated phosphonic acid is effected in only a few seconds when the metal oxide surface is exposed to the solution, for example is immersed in the solution, in order to bring about a macroscopically detectable change in the wetting property.

According to a preferred embodiment, the process is moreover distinguished by the fact that it furthermore comprises the following steps:
cleaning of the printing plate to remove ink (for example with the use of Eurostar, IPA or ethanol) and activation and/or initialization by exposure of the metal oxide surface to a UV light source;
removal of nonadhering compounds from the treated metal oxide surface; and
drying of the metal oxide surface with an anhydrous process gas, in particular with nitrogen.

Furthermore, the following process step can be carried out after the process step comprising cleaning:
coating of the surface of the printing area with fluorinated phosphonic acid molecules from ethanolic or aqueous solution.

The removal of nonadhering compounds can be effected in particular with an alcoholic solution, preferably with ethanol.

According to a preferred embodiment, the process is furthermore distinguished by the fact that the preparation of the reusable printing plate comprises the following steps for the preparation of a naturally oxidized titanium surface:
etching of the naturally oxidized titanium surface; and
production of a defined oxide film, in particular of a hydrophilic surface or of a lipophilic surface for dry offset printing ink.

Preliminary cleaning may include the step of rinsing with acetone, ethanol, isopropanol, ethyl acetate or another suitable organic solvent. One purpose is in particular the degreasing of the surface.

The metal oxide surface can then be exposed to an aqueous solution having the composition of one part by volume of 25% strength $NH_4OH$ solution and one part by volume of 30% strength $H_2O_2$ solution in four parts by volume of $H_2O$ at a temperature of about 60° C. for about the duration of 10 minutes. This step is particularly advantageous for a naturally oxidized titanium surface. One purpose is in particular oxidation of hydrocarbons present on the metal oxide surface.

Principal cleaning can be effected by etching of the metal oxide surface. The etching can be carried out through the use of a solution having the composition of one part by volume of 40% strength HF solution and three parts by volume of 30% strength $H_2O_2$ in twenty parts by volume of $H_2O$ at room temperature for the duration of about 1 minute. One purpose is in particular the ablation of a few individual metal oxide layers and the establishment of a defined roughness (of a defined RMS value or root mean square value) of the metal oxide surface.

According to a preferred embodiment, the process is furthermore distinguished by the fact that the production of an image on the printing area is effected by selective point-by-point supply of energy with the aid of electromagnetic radiation, in particular in the infrared spectral range, and that the erasing of the image is effected by supply of energy over a large area through the use of irradiation of the printing area with electromagnetic radiation, in particular in the ultraviolet spectral range.

Electromagnetic radiation for producing an image may be in the range from 150 to 1200 nanometers. In particular, the supply of energy can be effected in the infrared spectral range. Digital imaging can be effected through the use of a laser, preferably having a wavelength of about 1100 nanometers.

In a preferred embodiment, the image can be erased by a supply of energy over a large area for producing hydrophobic properties through the use of irradiation of the printing area with electromagnetic radiation. In particular, the irradiation over a large area can be effected in the ultraviolet spectral range. A preferred light source is an excimer emitter, in particular an ($Xe_2$) excimer emitter.

According to a preferred embodiment, the process is furthermore distinguished in that, after erasing of an image with the use of UV radiation, the printing area is treated with at least one fluorinated phosphonic acid.

According to a preferred embodiment, the process is furthermore distinguished in that, after printing on the print medium, cleaning of the printing area to remove printing ink, in particular with the use of a conventional ink cleaner, is carried out.

The cleaning of the printing area after printing on the print medium can be carried out with the use of a conventional ink cleaner or of a conventional detergent, of a surfactant-containing aqueous solution, for example the detergent sold under the name EUROSTAR.

The invention provides a reusable, in particular rewriteable or reimageable, printing plate having reliably reproducible behavior with respect to the imaging and erasing process. The production of an image or of a structure on the printing area is simple and reliable. It is not necessary for a monolayer of the fluorinated phosphonic acid to be established in a self-organizing manner on the metal oxide surface. The process for imaging therefore requires a shorter time for the provision of the printing plate according to the invention. The application of the abovementioned compounds within a period of a few seconds is sufficient for rendering the metal oxide surfaces sufficiently strongly hydrophobic or lipophobic, in particular for use in an offset printing process. In particular, the process according to the invention makes it possible to render rough metal oxide surfaces hydrophobic, said surfaces being produced in conventional industrial production processes.

In accordance with the invention, there is also provided a chemical compound, in particular amphiphilic molecules, with which reusable printing plates can be treated, i.e. brought into contact, wetted or (nano)coated and which converts the surface of the printing plate into a defined initial state for imaging, for example into a hydrophobic state (in wet offset printing) or a lipophobic state (in dry offset printing).

The invention also relates to the preparation or the synthesis of such a chemical compound.

The synthesis of a chemical compound according to the invention, namely of a fluorinated phosphonic acid, in particular of a semiperfluorinated alkylphosphonic acid or (partly) aromatic phosphonic acid, by the process according to the invention for the preparation of fluorinated phosphonic acid is based, in process steps b) and c), on the synthesis of a corresponding carboxylic ester by Metzger et al. (cf. Metzger, J. O. and Linker, U., Liebigs Ann. Chem., 1992, 209).

With the objects of the invention in view, there is concomitantly provided a process for the preparation of a chemical compound according to the invention, namely of a fluorinated phosphonic acid, in particular for the treatment of a reusable printing plate, which comprises the following process steps:

a) coupling of an alkenyl halide such as an alkenyl bromide, sn alkenyl chloride, or an alkenyl iodide, preferably an lkenyl bromide, with a monoalkyl phosphite or a dialkyl phosphite or a trialkyl phosphite to give an alkyl alkenylphosphonate, the monoalkyl phosphite or dialkyl phosphite being deprotonated and the trialkyl phosphite being dealkylated;
b) coupling of the alkyl alkenylphosphonate with an iodinated fluorohydrocarbon by reaction with an organic silver compound and/or tin halide to give fluorinated alkyl phosphonate;
c) deiodinization of the fluorinated alkyl phosphonate with the aid of an organic tin compound;
d) substitution of the fluorinated alkyl phosphonate by reaction with halogenated organic silicon compound to give fluorinated alkylsilyl phosphonate;
e) alcoholysis of the fluorinated alkylsilyl phosphonate to give a fluorinated phosphonic acid.

According to a preferred embodiment of the process according to the invention, the alkyl alkenylphosphonate is a dialkyl alkenylphosphonate, in particular a dibutyl alkenylphosphonate.

According to a preferred embodiment of the process according to the invention, the alkenyl bromide is a partly aromatic alkenyl bromide, and the alkyl alkenylphosphonate is a partly aromatic alkyl alkenylphosphonate.

According to a preferred embodiment of the process according to the invention, the deprotonation is effected with sodium.

According to a preferred embodiment of the process according to the invention, the iodinated fluorohydrocarbon is a fluorinated alkyl iodide or fluorinated, (partly) aromatic iodide, in particular a completely fluorinated (perfluoro-) alkyl iodide.

According to a preferred embodiment of the process according to the invention, the organic silver compound is silver(I) acetate and/or the tin halide is tin(II) chloride.

According to a preferred embodiment of the process according to the invention, the fluorinated alkyl phosphonate is a semiperfluorinated dialkyl alkylphosphonate.

According to a preferred embodiment of the process according to the invention, the organic tin compound is tributylstannane.

According to a preferred embodiment of the process according to the invention, the halogenated organic silicon compound is a trialkylsilyl halide, in particular trimethylsilyl bromide.

According to a preferred embodiment of the process according to the invention, the fluorinated alkylsilyl phosphonate is a di(trialkylsilyl) phosphonate, in particular a semiperfluorinated di(tributylsilyl) alkylphosphonate.

According to a preferred embodiment of the process according to the invention, the alcoholysis is effected by reaction with methanol.

According to a preferred embodiment of the process according to the invention, the fluorinated phosphonic acid is a fluorinated alkylphosphonic acid, in particular a semiperfluorinated alkylphosphonic acid, or a (partly) aromatic phosphonic acid.

A further or alternative process according to the invention for imaging of a reusable printing plate is distinguished by:
preparation of a reusable printing plate having a printing area, as described above with reference to a printing plate according to the invention, a fluorinated phosphonic acid, as described above with reference to a chemical compound according to the invention, being applied to the surface of the printing plate;
production of an image on the printing plate by selective point-by-point supply of energy; and
erasing of the image after printing on a print medium, in particular in an offset printing process, by supply of energy over a large area.

A further or alternative process according to the invention for imaging of a reusable printing plate is distinguished by:
synthesis of a fluorinated phosphonic acid, as described above with reference to a process for the preparation of a chemical compound according to the invention, and preparation of a reusable printing plate having a printing area, as described above with reference to a printing plate according to the invention, the fluorinated phosphonic acid being applied to the surface of the printing plate;
production of an image on the printing plate by selective point-by-point supply of energy; and
erasing of the image after printing on a print medium, in particular an offset printing process, by a supply of energy over a large area.

Other features which are considered as characteristic for the invention are set forth in the appended claims.

Although the invention is illustrated and described herein as embodied in a reusable printing plate, a printing press and a printing unit having the printing plate, a process for imaging the printing plate and a process for preparation of a fluorinated organic phosphonic acid, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWINGS

FIGS. 4a-4e show the synthesis of semiperfluorinated stearylphoshonic acid.

DESCRIPTION OF THE PREFERRED EMBODIMENTS

Figure 1:
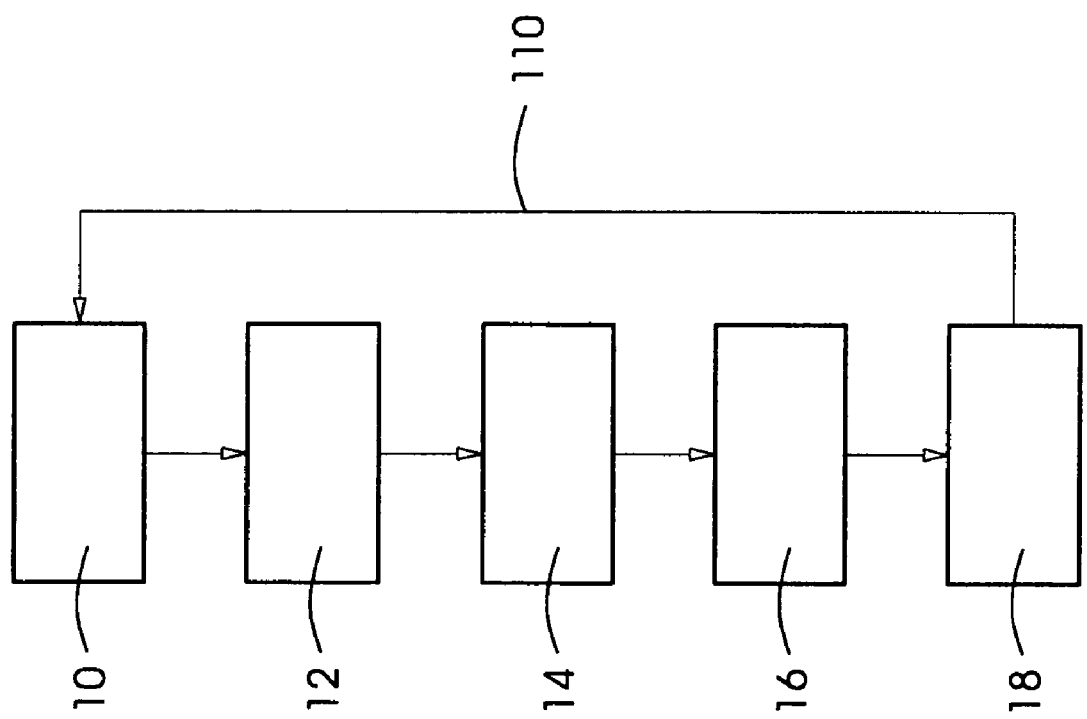
FIG. 1 is a sequence diagram of an advantageous embodiment of the process according to the invention for imaging of a reusable printing plate according to the invention.

Referring now to the figures of the drawings in detail and first, particularly, to FIG. 1 thereof, there is seen a sequence diagram of an advantageous embodiment of the process according to the invention for imaging of a reusable printing plate according to the invention.

In order initially to clean and to activate/initialize the titanium surface to be treated, for example in the form of a metal sheet, the surface is first exposed to light in the ultraviolet wavelength range in process step 10. The exposure is preferably effected for about 10 minutes with the use of a xenon excimer UV lamp (e.g. the lamp "Xeradex" from Radium) at a wavelength of 172 nanometers and with an intensity of 45 milliwatts per square centimeter.

In the course of a first preparation step to be carried out only once, metal surfaces, for example titanium surfaces, can initially be roughened for wet offset printing, a roughness (RMS or root mean square) of about 350 nanometers being preferred.

For dry offset printing, on the other hand, relatively smooth metal surfaces, for example surfaces of titanium sheets, are preferably used, a roughness (RMS or root mean square) of less than about 80 nanometers being preferred. If, instead, polyimide sheets coated with titanium by vapor deposition are used, a roughness (RMS or root mean square) of less than about 50 namometers is preferably chosen.

The process step of the preparation 12 of a reusable printing plate includes the application of the semiperfluorinated alkylphosphonic acid to the surface of the printing plate. The previously cleaned and simultaneously activated/initialized titanium surface is immersed, without substantial delay, in a solution which contains the abovementioned chemical compound in a suitable concentration. The titanium surface is preferably immersed in 1 mM ethanolic solution of perfluorinated alkylphosphonic acid for the duration of about 10 seconds. The immersion bath is thus of short duration, so that the preparation process advantageously can be carried out in a short time.

It is furthermore possible to provide a spray apparatus or a roll-application apparatus for applying the solution to the surface, instead of the immersion bath. The roll-application of the solution advantageously also results in the solution being thoroughly mixed close to the surface, with the result that the slow, diffusion-controlled movement of the semiperfluorinated alkylphosphonic acid molecules toward the titanium surface is superposed by a faster mixing movement.

Cleaning of the treated titanium surface can be effected in the course of process step 12 by rinsing with ethanol, which removes the nonadhering compounds. The cleaned titanium surface can then be completely dried using an anhydrous process gas, a so-called dry process gas, for example nitrogen.

Through the use of the immersion bath, the surface of the printing plate becomes hydrophobic and lipophilic for wet offset printing ink or lipophobic for dry offset printing ink.

Titanium surfaces prepared or provided in this manner can be digitally imaged using infrared light sources. In the process step of imaging 14, the titanium surface is imaged, for example, using an infrared laser at a wavelength between about 810 and 1100 nanometers. In an advantageous embodiment, the light source used is an IR laser having a power of from about 1 to 5 watts, at an imaging speed of the surface of from about 1 to 2 meters per second and a flux of from about 30 to 40 joules per square centimeter. Local, selective, digital imaging can be carried out through the use of 30 micrometer light spots ($1/e^2$ decay).

A printing plate capable of functioning can be obtained with incident radiation of more than 15 joules/square centimeter. Particularly good quality is achieved from about 30 joules/square centimeter.

In the process step of printing 16, reproduction of the subject on a print medium is effected by an offset printing process, for example on a Quickmaster printing press from Heidelberger Druckmaschinen AG. After the printing, the titanium surface can optionally be cleaned by contact with a solution of suitable composition to remove printing ink. In an advantageous embodiment, ink cleaner from EUROSTAR is used.

In the process step of erasing 18, the titanium surface is exposed to ultraviolet light having a wavelength of about 172 nanometers over a large area for about the duration of 5 minutes. The light source used is a xenon excimer UV emitter (for example the emitter "Xeradex" from Radium) having an optical power of 5 watts at an electrical power of 20 watts.

Furthermore, the surface can be erased by the action of an atmospheric-pressure plasma or by mechano-chemical ablation of a few nanometers of the surface.

A repetition 110 of the individual steps, beginning with the step of cleaning/of activation/initialization 10 of the reusable printing plate, is now possible.

The chemical surface condition after a preparation according to the invention and imaging of the titanium surface can be determined by XP and IR spectroscopic investigations. It is found that no semiperfluorinated alkylphosphonic acid molecules are detectable within the laser-imaged regions of the surface.

Figure 2:
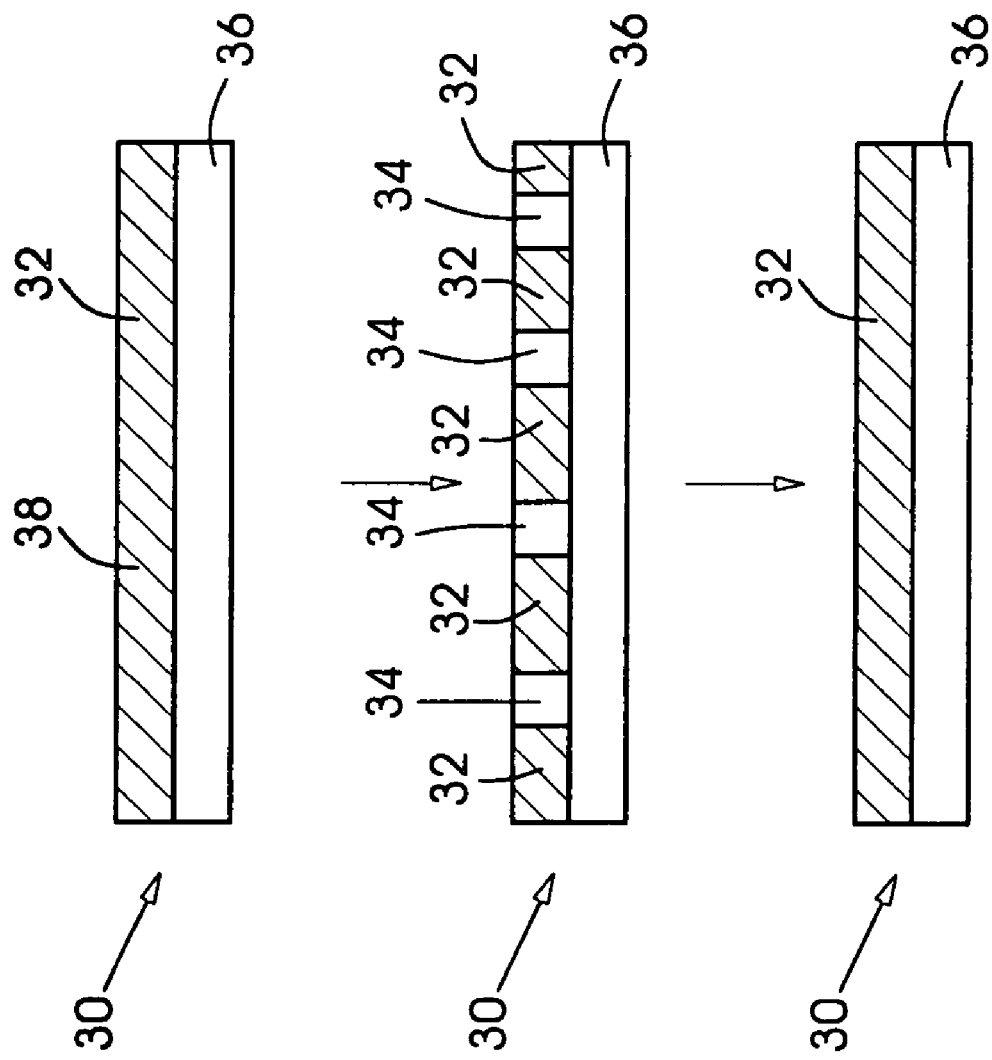
FIG. 2 is a diagrammatic, sectional view of the structuring of a reusable wet offset printing plate according to the invention by the process according to the invention.

FIG. 2 is a schematic diagram of the structuring of a reusable wet offset printing plate 30 according to the invention through the use of the process according to the invention. The reusable wet offset printing plate 30 has a metal surface 36 which is treated with at least one fluorinated phosphonic acid in the form of a (nano)layer 38.

FIG. 2 shows three states of the printing plate 30, the order of which as a function of time is indicated by the arrows.

First, the printing plate 30 is present with a large hydrophobic and lipophilic printing area 32 with respect to wet offset printing ink. By local, point-by-point, selective imaging, hydrophilic regions 34 are produced or exposed on the surface of the printing plate 30. The surface thus has a structure including hydrophobic regions 32 and hydrophilic regions 34, so that it can be used for printing, in particular in a wet offset printing process.

By irradiation of the surface of the printing plate 30 over a large area and treatment with a fluorinated phosphonic acid, it is ensured that the printing plate 30 once again has a large hydrophobic and lipophilic printing area 32 with respect to a wet offset printing ink.

Figure 3:
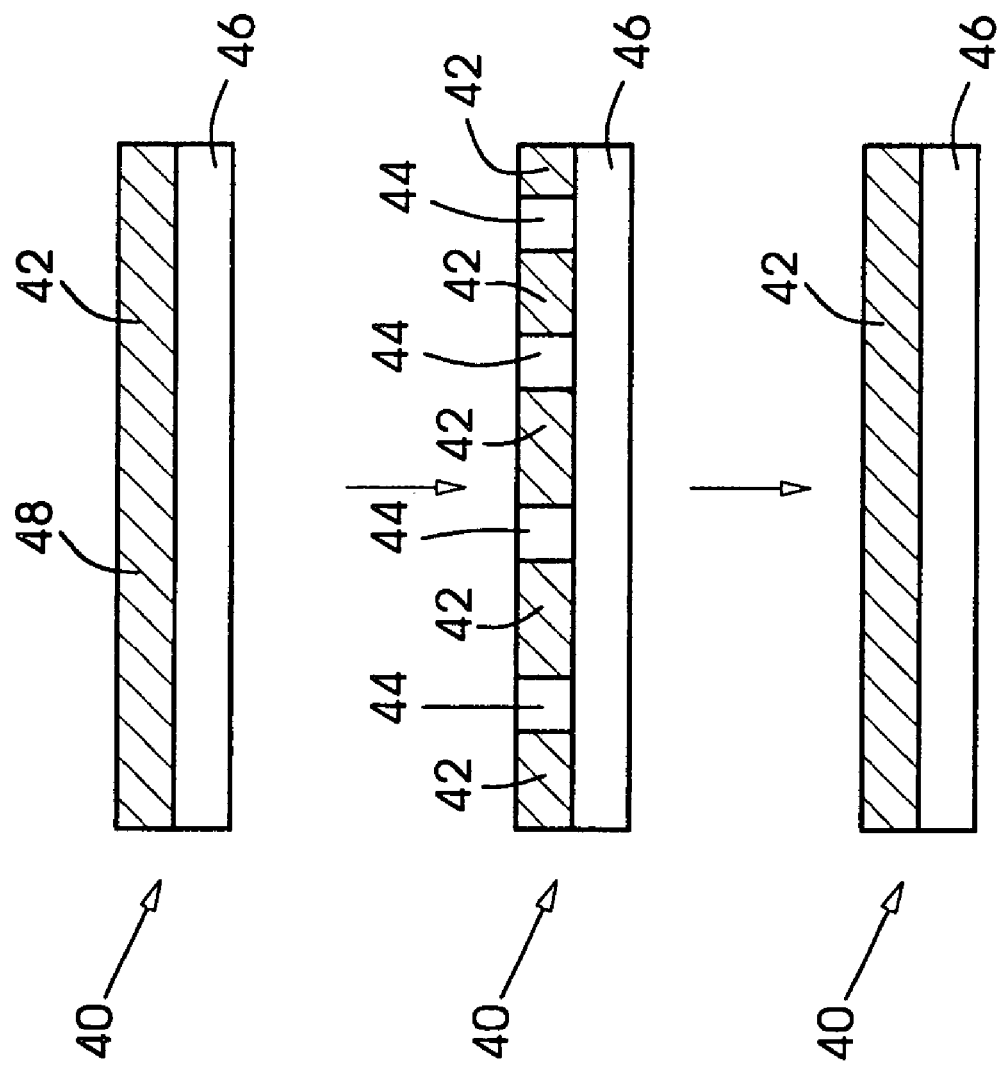
FIG. 3 is a sectional view of the structuring of a reusable dry offset printing plate according to the invention by the process according to the invention.

FIG. 3 is a schematic diagram of the structuring of a reusable dry offset printing plate 40 according to the invention through the use of the process according to the invention. The reusable dry offset printing plate 40 has a metal surface 46 which is treated with at least one fluorinated phosphonic acid in the form of a (nano)layer 48.

FIG. 3 shows three states of the printing plate 40, the order of which as a function of time is indicated by the arrows.

First, the printing plate 40 is present with a large lipophobic printing area 42 with respect to a dry offset printing ink. By local, point-by-point, selective imaging, lipophilic regions 44 are produced or exposed on the surface of the printing plate 40. The surface thus has a structure including lipophobic regions 42 and lipophilic regions 44, so that it can be used for printing, in particular in a dry offset printing process.

By irradiation of the surface of the printing plate 40 over a large area and treatment with a fluorinated phosphonic acid, it is ensured that the printing plate 40 once again has a lipophobic printing area 42 over a large area with respect to a dry offset printing ink.

Below, the preparation or synthesis of a fluorinated phosphonic acid is described for the example of semiperfluorinated stearylphosphonic acid (the complete name is: (18,18,18,17,17,16,16,15,15,14,14,13,13,12,12-pentadecylfluorooctadecylphosphonic acid) with reference to FIG. 4.

The following abbreviations are used:
b.p.: boiling point
$^{1}$H-/$^{13}$C-/$^{31}$P-NMR: nuclear magnetic resonance spectrometry s, d, t, m: singlet, doublet, triplet, multiplet in NMR $R_f$: retention factor (consecutive value in thin-layer chromatogram)

The numbering a) to e) shown in the Fig. corresponds to process steps a) to e) in the preparation of the chemical compound (cf. also numbering in the corresponding c(18,18,18,17,17,16,16,15,15,14,14,13,13,12,12-pentadecylfluorooctadecylphosphonic acid) laim).

The synthesis described is based on the synthesis of the corresponding carboxylic ester by Metzger et al. (Metzger, J. O. and Linker, U., Liebigs Ann. Chem., 1992, 209).

Synthesis of dibutyl 10-undecenylphosphonate (cf. FIG. 4, I or a)): first 8.4 g of dibutyl phosphite and then 10 g of bromoundecene are added dropwise to 0.9 g of sodium in boiling petroleum ether and stirring is effected overnight. The salt formed is separated from the solution and the filtrate is evaporated down in a rotary evaporator and dried. The liquid is distilled.

$C_{19}H_{39}O_3P$ (346.2 g mol$^{-1}$), colorless liquid, b.p.: 180° C./1 mbar.

$^{1}$H-NMR (CDCl$_3$, 300 MHz): δ [ppm]=0.91 (t, 6H, —CH$_3$), 1.25-1.49 (m, 18H, alkyl-H), 1.50-1.75 (m, 8H, alkyl-H), 2.01 (dt, 2H=CH—CH$_2$), 3.98 (m, 4H, —O—CH$_2$), 4.88-5.00 (dd, 2H, H$_2$C=), 5.80 (ddt, 1H, H$_2$C=CH—).

$^{13}$C-NMR (CDCl$_3$, 75 MHz): δ [ppm]=13.6 (—CH$_3$), 18.8 (—CH$_2$—CH$_3$), 33.8 (=CH—CH$_2$—), 65.1 (—O—CH$_2$—), 114.2 (H$_2$C=), 139.2 (=CH—).

Synthesis of dibutyl 10-iodo-semiperfluorostearylphosphonate (cf. FIG. 4, II or b)): 49 mg of silver acetate and 1.35 g of tin(II) chloride are added to 50 ml of methanol (p.a.) under a countercurrent of N$_2$ and stirring is effected for about 30 minutes. 0.64 g of ester and 1.5 g of iodide are then simultaneously added dropwise and likewise countercurrently, and stirring is effected until the color changes to yellowish. For purification, the solvent is removed and the residue is obtained over a silica gel column using petroleum ether and ethyl acetate in the ratio 3:1 and is then purified by distillation.

$C_{26}H_{39}F_{15}IO_3P$ (842.1 g mol$^{-1}$), colorless liquid, b.p.: 185-190° C./3.4·10$^{-1}$ mbar.

$^{1}$H-NMR (CDCl$_3$, 300 MHz): δ [ppm]=0.92 (t, 6H, —CH$_3$), 1.20-1.45 (m, 16H, alkyl-H), 1.58-1.76 (m, 10H, alkyl-H), 2.83 (m, 2H, —CF$_2$—CH$_2$—), 4.00 (m, 4H, —O—CH$_2$), 4.31 (m, 1H, CH).

$^{13}$C-NMR (CDCl$_3$, 75 MHz): δ [ppm]=14.0 (—CH$_3$), 18.5 (—CH$_2$—CH$_3$), 20.6 (—CH-?), 32.4 (—O—CH$_2$—CH$_2$—), 41.2 (t, —CF$_2$—CH$_2$—), 64.9 (—O—) CH$_2$—).

Synthesis of dibutyl semiperfluorostearylphosphonate (cf. FIG. 4, III or c)): 0.7 ml of tributylstannane is added to 1.35 g of the ester (II) dissolved in 20 ml of toluene (p.a.) and stirring is effected for 48 h. The solvent is removed and the residue is taken up in ether. A few iodine crystals are added until a red color appears. After addition of 0.63 g of potassium fluoride and a little crown ether ([18]crown-6), stirring is effected overnight. The residue is taken up in ether, filtered, and washed with a little ether. The organic phase is evaporated down in a rotary evaporator and dried. The pure product is obtained over a silica gel column using petroleum ether (40/60) in ethyl acetate (95:5).

$C_{26}H_{40}F_{15}O_3P$ [716 g mol$^{-1}$], colorless liquid, b.p. (sublimation point): 170° C./2.1·10$^{-2}$ mbar.

$^{1}$H-NMR (CDCl$_3$, 300 MHz): δ [ppm]=0.92 (t, 6H, —CH$_3$), 1.20-1.45 (m, 20H, alkyl-H), 1.53-1.76 (m, 12H, alkyl-H), 2.02 (m, 2H, —CF$_2$—CH$_2$—), 3.99 (m, 4H, —O—CH$_2$)

$^{13}$C-NMR (CDCl$_3$, 75 MHz): δ [ppm]=13.3 (—CH$_3$), 18.5 (—CH$_2$—CH$_3$) 30.4 (t, —CF$_2$—CH$_2$—), 32.4 (—O—CH$_2$—CH$_2$—), 64.9 (—O—CH$_2$—).

Synthesis of semiperfluorostearylphosphonic acid (cf. FIG. 4, IV or d) and e)): 0.38 g of ester (III) in dried chloroform is initially introduced, 0.15 ml of trimethylsilyl bromide is added and stirring is effected for 48 h. After the solvent and the remaining bromide have been removed in vacuo, the residue is dried, a few ml of methanol are added and stirring is effected for 1 h at room temperature. The solvent is stripped off again and dried in vacuo. The residue formed is pure.

$C_{18}H_{24}F_{15}O_3P$ [604 g mol$^{-1}$], colorless liquid.

$^{1}$H-NMR (CDCl$_3$, 300 MHz): δ [ppm]=1.22-1.28 (m, 14H, alkyl-H), 1.47-1.53 (m, 6H, alkyl-H), 2.05 (m, 2H, —CF$_2$—CH$_2$—)

$^{13}$C-NMR (CDCl$_3$, 75 MHz): δ [ppm]=19.7-29.0 (alkyl-C), 30.2 (t, —CF$_2$—CH$_2$—).

The synthesized semiperfluorinated stearylphosphonic acid is particularly suitable for the treatment of printing surfaces.

A general formula of the preferred compound for the treatment of a reusable printing plate (straight-chain and, by way of example, singly branched) can be stated as follows:

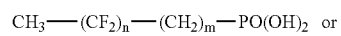

-continued

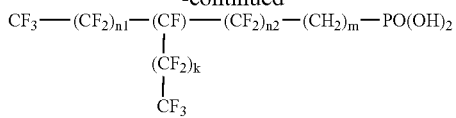

and the ammonium, calcium, potassium, and sodium salts thereof, wherein n, $n_1$, $n_2$, m and k are each an integer from 0 to 30, provided that the sum of m, n, and, when present $n_1$, $n_2$, m and k is an integer from 8 to 30.

Single or multiple branches in the alkyl chain are also possible.

Instead of the $PO(OH)_2$ group (which may also be referred to as an anchor group to the printing surface), it is also possible to provide salts thereof, e.g. potassium salt, sodium salt, ammonium salt or calcium salt.

The phosphonic acids, phosphonates, phosphates, salts of the phosphates and salts of the phosphonates form further possible anchor groups.

This application claims the priority, under 35 U.S.C. § 119, of German Patent Application 10 2004 034 581.3, filed Jul. 16, 2004; the entire disclosure of the prior application is herewith incorporated by reference.

We claim:

1. A reusable dry offset printing plate, comprising:
   a dry offset printing area; and
   a metal oxide surface made hydrophobic with at least one fluorinated phosphonic acid on said printing area;
   said fluorinated phosphonic acid being selected from the group consisting of:
   a fluorinated alkylphosphonic acid,
   a semiperfluorinated alkylphosphonic acid,
   a partly aromatic acid, and
   a fluorinated phosphonic acid having single or multiple branches in the alkyl chain and a number of carbon atoms being greater than or equal to 8 and less than or equal to 30.

2. The reusable printing plate according to claim 1, wherein said fluorinated phosphonic acid is a fluorinated organic phosphonic acid having 8 to 30 carbon atoms.

3. The reusable printing plate according to claim 1, wherein said metal oxide surface is selected from the group consisting of naturally oxidized titanium surface, naturally oxidized stainless steel surface, naturally oxidized aluminum surface, titanate ($TiO_2$) and zirconate ($ZrO_2$).

4. The reusable printing plate according to claim 1, wherein said treated printing area is lipophilic for dry offset printing ink.

5. A printing unit, comprising at least one reusable printing plate according to claim 1.

6. A printing press, comprising at least one printing unit according to claim 1.

7. A process for imaging of a reusable printing plate, which comprises the following steps:
   preparation of a reusable printing plate according to claim 1;
   production of an image on the printing plate by selective point-by-point supply of energy;
   printing the image on at least one print medium; and
   erasing the image by supply of energy over a large area.

8. The reusable printing plate according to claim 1, wherein said dry offset printing area is a polyimid sheet coated with titanium by vapor deposition.

9. A reusable wet offset printing plate, comprising:
   a wet offset printing area; and
   a metal oxide surface made hydrophobic with at least one fluorinated phosphonic acid on said printing area;
   said fluorinated phosphonic acid being a partly aromatic acid.

* * * * *